United States Patent [19]

Mayer et al.

[11] 4,187,306
[45] Feb. 5, 1980

[54] BENZODIAZEPINE-DIONES, A PROCESS FOR THEIR PRODUCTION AND THEIR USE AS MEDICAMENTS

[75] Inventors: Karl H. Mayer; Helmut Heitzer, both of Leverkusen; Friedrich Hoffmeister, Wuppertal; Arend Heise, Wuppertal; Stanislav Kazda, Wuppertal, all of Fed. Rep. of Germany

[73] Assignee: Bayer Aktiengesellschaft, Leverkusen, Fed. Rep. of Germany

[21] Appl. No.: 922,419

[22] Filed: Jul. 6, 1978

[30] Foreign Application Priority Data

Jul. 26, 1977 [DE] Fed. Rep. of Germany ....... 2733681
Dec. 30, 1977 [DE] Fed. Rep. of Germany ....... 2758875

[51] Int. Cl.² ........................................... C07D 471/04
[52] U.S. Cl. .............................. 424/251; 260/239.3 P; 544/290
[58] Field of Search .................. 260/239.3 P; 424/251

[56] References Cited

U.S. PATENT DOCUMENTS 3,651,046   3/1972   Derieg et al. ................. 260/239.3 P

OTHER PUBLICATIONS

Harrison et al., "J. Heterocyclic Chemistry", vol. 14, No. 7, pp. 1191–1196 (1977), (Nov.).
Chemical Abstracts, vol. 88, Item 105281n, abstracting Harrison et al., in "J. Heterocyclic Chemistry", (1977), vol. 14, No. 7, pp. 1191–1196 (English).

*Primary Examiner*—Alan L. Rotman
*Assistant Examiner*—Robert T. Bond
*Attorney, Agent, or Firm*—Sprung, Felfe, Horn, Lynch & Kramer

[57] ABSTRACT

The invention covers compounds of the formula

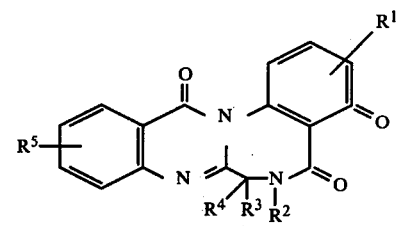

in which $R^1$ and $R^5$ each represents 0, 1, 2, 3 or 4 of the following substituents: alkyl, hydroxyl, acyloxy, alkoxy, nitro, amino, alkylamino, dialkylamino, acylamino, acylalkylamino, alkoxycarbonylamino, halogen, trifluoromethyl, cyano, carboxyl, alkoxycarbonyl, aminocarbonyl, alkylaminocarbonyl, dialkylaminocarbonyl, aminosulphonyl, alkylaminosulphonyl, dialkylaminoamino, $R^2$ is hydrogen, optionally substituted alkyl, aralkyl or aryl or heterocyclo-alkyl, acyl or alkoxycarbonyl, and $R^3$ and $R^4$ are each hydrogen, or optionally substituted alkyl, aralkyl, aryl or hetero-aryl, are useful as medicaments which have an action on the central nervous system, in particular as, for example, tranquilizers and/or antiamnesics. Also included in the invention are methods for preparing said compounds, compositions containing them and methods for the use of said compounds and compositions.

21 Claims, No Drawings

BENZODIAZEPINE-DIONES, A PROCESS FOR THEIR PRODUCTION AND THEIR USE AS MEDICAMENTS

The present invention relates to certain new 6,7-dihydro-5H,13H-quinazolino[3,2,-a][1,4]benzodiazepine-5,13-diones, to a process for their production and their use as medicaments, preferably as substances which have an action on the central nervous system, in particular as cerebral-antiischaemic or antiamnesic active compounds, as active compounds which improve the learning ability, performance and memory, tranquilisers and as analgesic or anti-pyretic active compounds.

The present invention provides compounds which are 6,7-dihydro-5H,13H-quinazolino[3,2-a][1,4]benzodiazepin-5,13-diones of the following general formula (I) or their salts:

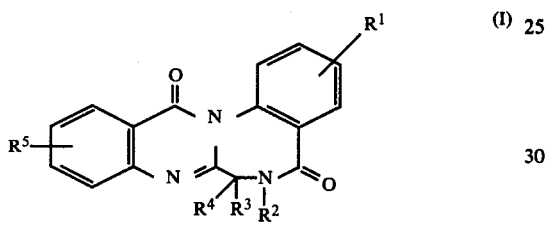

in which
$R^1$ and $R^5$ are the same or different and each represents 0, 1, 2, 3 or 4 substituents which are the same or different and each of which is alkyl, hydroxyl, acyloxy, alkoxy, nitro, amino, alkylamino, dialkylamino, heterocycloalkyl containing at least one nitrogen atom in the ring through which it is bonded, acylamino, acylalkylamino, alkoxycarbonylamino, halogen, trifluoromethyl, cyano, carboxyl, alkoxycarbonyl, aminocarbonyl, alkylaminocarbonyl, dialkylaminocarbonyl, aminosulphonyl, alkylaminosulphonyl, dialkylaminosulphonyl, alkylaminocarbonylamino and dialkylaminocarbonylamino,
$R^2$ is hydrogen, optionally substituted alkyl, aralkyl or aryl or heterocyclo-alkyl, acyl or alkoxycarbonyl, and
$R^3$ and $R^4$ are the same or different and each is hydrogen, optionally substituted alkyl, aralkyl which is optionally substituted in the aryl moiety, optionally substituted aryl or heteroaryl, and their pharmacologically acceptable salts with inorganic or organic acids.

In a further aspect the present invention provides a process for the preparation of a compound according to the present invention in which a 2-alkyl-3-aryl-4H-quinazolin-4-one of the following general formula (II) or a salt thereof:

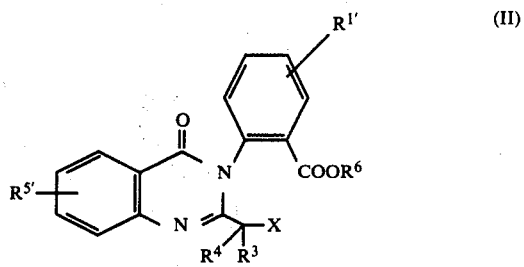

in which
$R^3$ and $R^4$ have the same meaning as defined hereinbefore in formula I,
$R^{1'}$ and $R^{5'}$ are the same or different and each represents 0, 1, 2, 3 or 4 substituents which are the same or different and each of which is alkyl, hydroxyl, acyloxy, alkoxy, nitro, dialkylamino, heterocycloalkyl containing at least one nitrogen atom in the ring through which it is bonded, acylamino, acylalkylamino, alkoxycarbonylamino, halogen, trifluoromethyl, cyano, alkoxycarbonyl, dialkylaminocarbonyl, aminosulphonyl, alkylaminosulphonyl, dialkylaminosulphonyl and dialkylaminocarbonylamino,
$R^6$ is hydrogen, alkyl, aralkyl or aryl and
X is a leaving group which can be easily replaced nucleophillically, such as halogen or alkylsulpho, aralkylsulpho or arylsulpho, is reacted with an amine of the following general formula (III) or a salt thereof:

$$H_2N-R^{2'} \qquad (III)$$

in which
$R^{2'}$ is hydrogen, optionally substituted alkyl, aralkyl, heterocyclic-alkyl or aryl, usually in the presence of inert solvent which is desirably an organic solubilising agent, and optionally in the presence of an acid-binding agent generally at a temperature of from 20° to 250° C., so as to produce a corresponding compound of formula I, and in the case of a compound of formula I in which $R^1$ and/or $R^5$ is amino, alkylamino, carboxyl, aminocarbonyl, alkylaminocarbonyl or alkylaminocarbonylamino, a said corresponding compound of formula I in which $R^1$ and/or $R^5$ is nitro or acylamino acylalkylamino, alkoxycarbonyl, and/or cyano or amino, respectively is converted thereto, and in the case of a compound of formula I in which $R^2$ is acyl or alkoxycarbonyl a said corresponding compound of formula I in which $R^2$ is hydrogen is converted thereto, conveniently by acylation using a carboxylic acid -chloride, sulphonic acid -chloride, or carbonic acid ester-chloride or a carboxylic acid anhydride or a pyrocarbonic acid ester.

The reaction of the 2-alkyl-3-aryl-4H quinazolin-4-one of the formula (II) with an amine of the formula (III) so as to produce the 6,7-dihydro-5H,13H-quinazolino[3,2-a][1,4]benzodiazepine-5,13-diones of the formula (I) proceeds in 2 reaction steps via the intermediate stages IV and/or V, which can be optionally isolated:

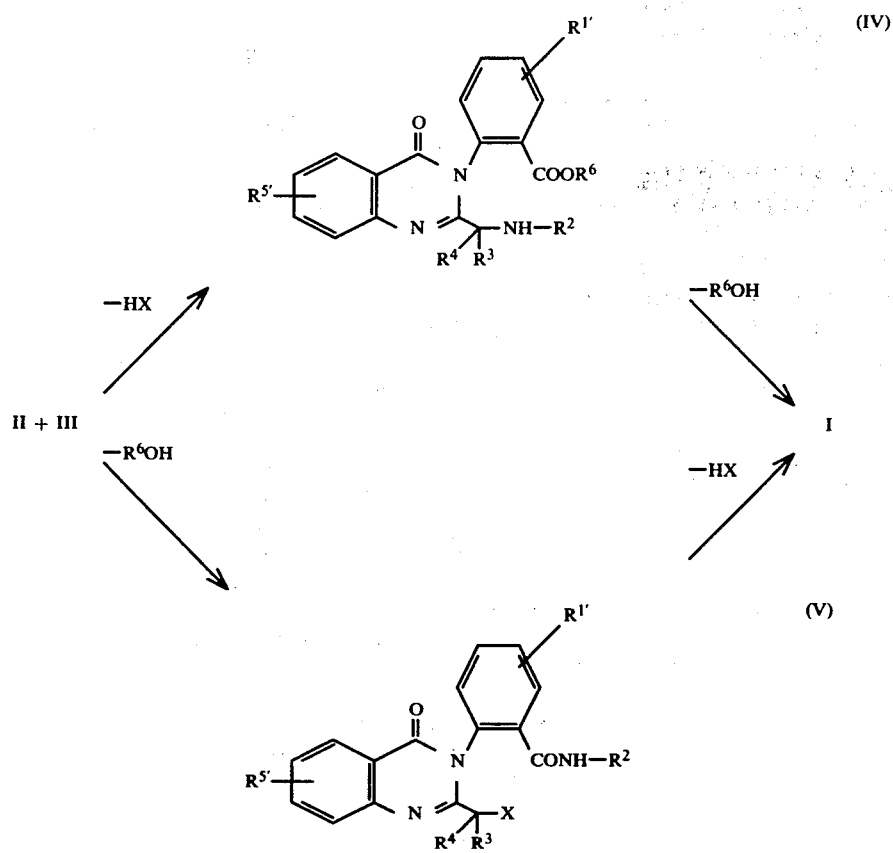

Surprisingly, the benzodiazepine compounds according to the invention exhibit very powerful actions on the central nervous system, in particular they have very good cerebral-antiischaemic or antiamnesic properties, the property of improving learning ability, performance and memory and tranquilising, analgesic or antipyretic properties.

Examples of reactions of individual reactants which can be used according to the invention are shown in the following reaction equation:

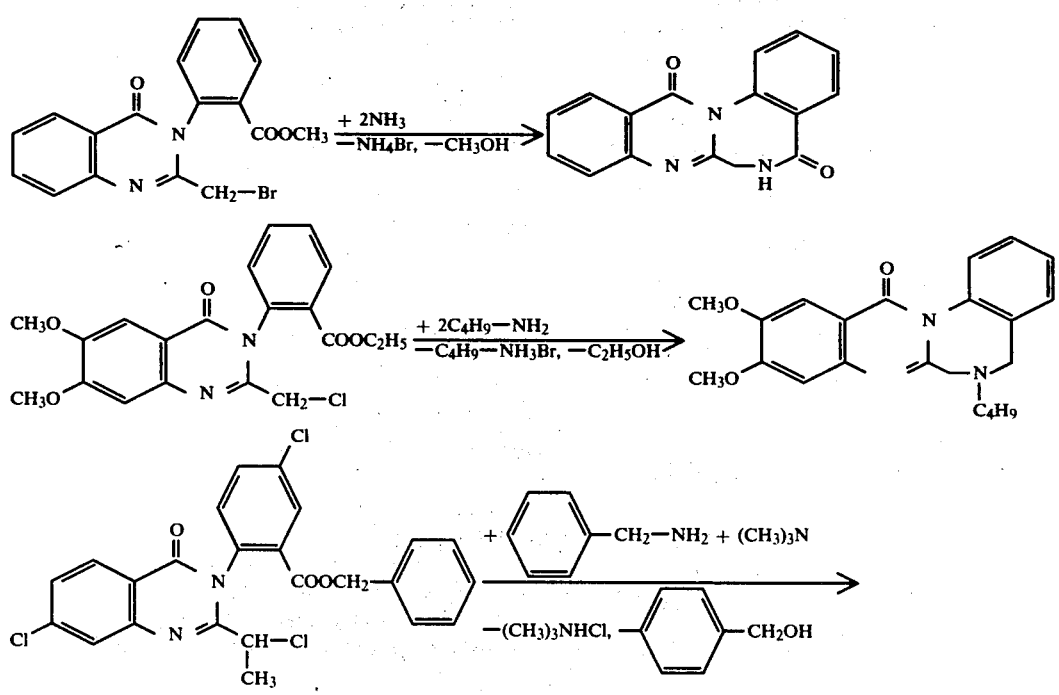

-continued
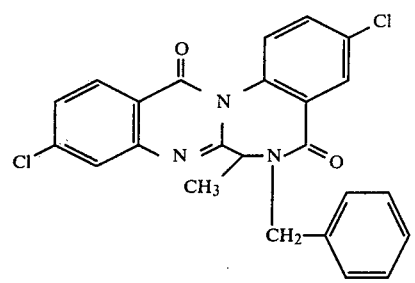
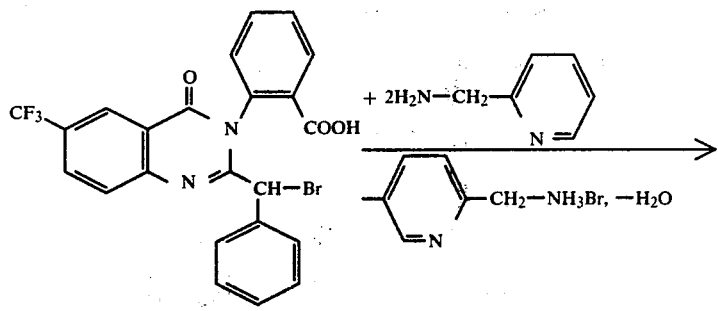
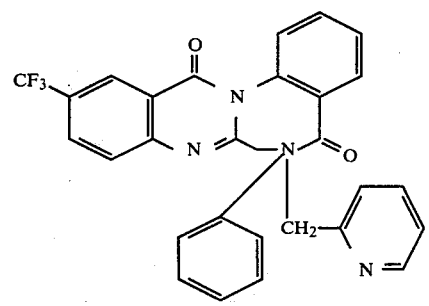
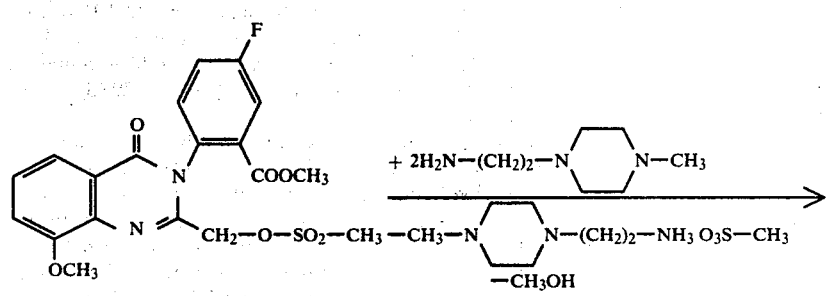
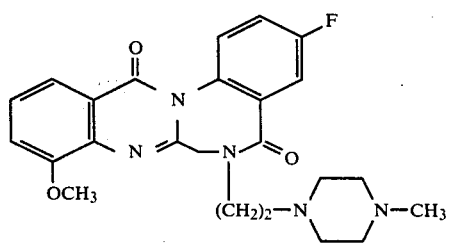
Examples of further reaction steps which can be optionally subsequently carried out:
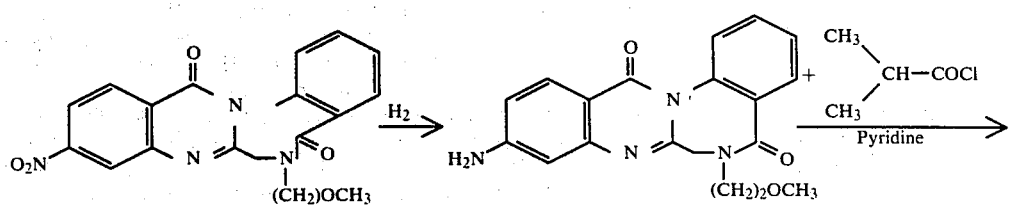

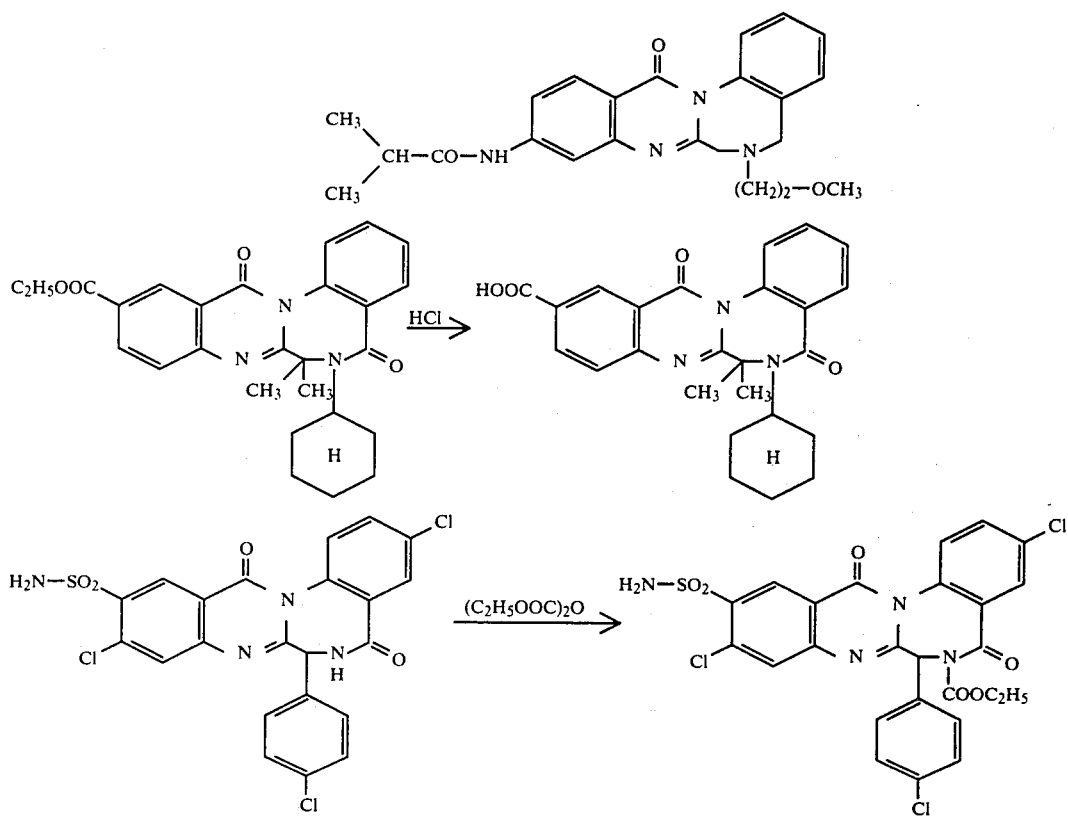

In formula (I), $R^1$ and $R^5$ preferably represent 0, 1 or 2 substituents each of which is alkyl, hydroxyl, alkoxy, nitro, amino, dialkylamino, acylamino, alkoxycarbonylamino, halogen, trifluoromethyl, carboxyl, alkoxycarbonyl, aminocarbonyl, dialkylaminocarbonyl, aminosulphonyl and dialkylaminosulphonyl, halogen representing, in particular, fluorine, chlorine and bromine and the alkyl, alkoxy and acyl radicals mentioned containing 1 to 4 carbon atoms, in particular 1 or 2 carbon atoms.

Heterocycloalkyl $R^1$ or $R^5$ is preferably a from 4- to 7-membered, particularly 5- to 6-membered ring, optionally containing a further heteroatom which is O, S, or N (in the form of NH or N-alkyl).

$R^3$ preferably represents hydrogen and $R^4$ preferably represents hydrogen, alkyl having from 1 to 16, in particular from 1 to 8, carbon atoms, aralkyl having from 1 to 6 carbon atoms in the alkyl moiety and preferably mono- or bi-cyclic carbocyclic in the aryl moiety, in particular benzyl or phenylethyl, aryl in the form of phenyl or heteroaryl in the form of a 5-membered or 6-membered heterocyclic system having from 1 to 3 heteroatoms from the group comprising nitrogen, oxygen and/or sulphur. Possible substituents in the aryl moiety of aralkyl and of aryl are halogen in particular bromine and chlorine, trifluoromethyl, hydroxyl, alkoxy and nitro.

$R^6$ preferably represents alkyl having 1 or 2 carbon atoms, benzyl or phenyl and X preferably represents halogen, in particular bromine or chlorine, or methylsulpho, phenylsulpho or 4-methylphenylsulpho.

The 2-alkyl-3-aryl-4H-quinazolin-4-ones of the formula II to be used as starting materials are known or can be prepared by known processes (compare J. Amer. Chem. Soc. 68 (1946), 542/J. org. Chem. 14 (1949), 967/J. Gen. Chem. (English translation) 30 (1960), 2333 and 34 (1964), 848/Chem. Abstr. 52 (1958), 9147/J. pr. Chem. (4) 14 (1961), 84/Arzneimittelforschung 13 (1963) 688/J. Med. Chem. 20 (1977), 379/Synthesis 1977, 309).

In detail, examples which may be mentioned are: 2-chloromethyl-3-(2-methoxycarbonyl-phenyl)-4H-quinazolin-4-one, 2-bromo-methyl-3-(2-methoxycarbonyl-phenyl)-4H-quinazoline-4-one, 2-chloromethyl-3-(2-ethoxycarbonyl-phenyl)-6-chloro-4H-quinazolin-4-one, 2-bromomethyl-3-(2-carboxy-phenyl)-4H-quinazolin-4-one, 2-chloromethyl-3-(2-methoxycarbonyl-5-chlorophenyl)-7-chloro-4H-quinazolin-4-one, 2-methylsulphomethyl-3-(2-ethoxycarbonylphenyl)-6-trifluoromethyl-4H-quinazolin-4-one, 2-phenylsulphomethyl-3-(2-methoxycarbonylphenyl)-8-methoxy-4H-quinazolin-4-one, 2-fluoromethyl-3-(2-methoxycarbonyl-phenyl)-6-fluoro-4H-quinazolin-4-one, 2-chloromethyl-3-(2-ethoxycarbonyl-phenyl)-6,7-dimethoxy-4H-quinazolin-4-one, 2-bromomethyl-3-(2-butoxycarbonyl-phenyl)-6,7,8-trichloro-4H-quinazolin-4-one, 2-(1-chloroethyl)-3-(2-methoxycarbonyl-phenyl)-6-dimethylamino-4H-quinazolin-4-one, 2-(α-bromobenzyl)-3-(2-carboxy-phenyl)-6-aminosulphonyl-7-chloro-4H-quinazolin-4-one, 2-(α-bromofurfuryl)-3-(2-benzyloxycarbonyl-4,6-dichlorophenyl)-4H-quinazolin-4-one and 2-(2-bromopropyl)-3-(2-methoxycarbonyl-4-trifluoromethylphenyl)-6-nitro-4H-quinazolin-4-one.

In the formula (I) $R^2$ preferably represents an optionally substituted alkyl radical having from 1 to 10, in particular from 1 to 6, carbon atoms, an optionally substituted aralkyl radical having from 1 to 6 carbon atoms in the alkyl moiety, in particular benzyl or phenethyl, an optionally substituted phenyl radical or a heterocycloalkyl radical having from 1 to 6 carbon atoms in the alkyl moiety and from 4 to 8 ring members and from 1 to 3 heteroatoms from the group comprising nitrogen, oxygen and/or sulphur in the hetero-aryl moiety, to which a phenyl ring can also be fused.

Possible substituents when $R^2$=alkyl or hydroxyl, alkoxy, amino, alkylamino, dialkylamino, acylamino, alkoxycarbonylamino, trifluoromethyl, cyano, carboxyl, alkoxycarbonyl, aminocarbonyl, alkylaminocarbonyl, dialkylaminocarbonyl, alkylaminocarbonylamino and sulpho, it also being possible for carboxyl and sulpho groups to be present in the form of salts with inorganic and organic acids, the dialkylamino moiety or group being in each case optionally replaced by a from 4- to 8-membered heterocycloalkyl containing at least one nitrogen atom in the ring via which it is bonded and optionally containing a further optionally substituted hetero-atom which is oxygen or sulphur or NH, N-alkyl, N-acyl or N-alkoxycarbonyl. Alkyl, alkoxy and acyl radicals mentioned in the possible substituents preferably contain from 1 to 4, in particular 1 or 2, carbon atoms.

Possible substituents when $R^2$=aralkyl or phenyl are halogen, in particular chlorine and bromine, trifluoromethyl, hydroxyl, alkoxy, nitro and alkyl, in the aryl moiety in each case.

The primary amines of the formula (III) to be used as starting materials are known or can be prepared by known processes.

Specific examples which may be mentioned are: methylamine, isobutylamine, 2-ethylhexylamine, 4-methylcyclohexylamine, 2-norbornylamine, allylamine, propargylamine, propylenediamine, 1-amino-2-diethylaminoethane, ethanolamine, 3-ethoxypropylamine, aminoacetic acid ethyl ester, aminopropionitrile, sodium aminoethanesulphonate, trifluoromethylethylamine, 2,4-dichlorobenzylamine, 4-chlorophenylethylamine, 3-ethoxyaniline, 4-diethylaminoaniline, 2-aminomethylfurane, 4-aminomethylpyridine, N-amino-ethyl-N'-methylpiperazine, N-aminobutyl-thiomorpholine 1,1-dioxide, 1-aminomethylisoquinoline and 1-aminopropyl-1,2,3-triazole.

In the formulae (I), (II) and (III), and correspondingly also (IV) and (V), alkyl represents, for example, methyl, ethyl, n- or iso-propyl, n-, iso- or tert.-butyl, n- or iso-hexyl, decyl, hexadecyl, allyl, propargyl or cyclohexyl.

Alkoxy represents, for example, methoxy, ethoxy, n- or iso-propoxy, n-, iso- or tert.-butoxy, allyloxy or cyclobutoxy.

Alkylamino and dialkylamino represent, for example, methylamino, dimethylamino, ethylamino, diethylamino, methylethylamino, n- or iso-propylamine, n-, iso- or tert.-butylamino, n- or iso-dipropylamino, n-, iso- or tert.-dibutylamino, allylamino or diallylamino. Heterocycloalkyl represents, for example, pyrrolidino, piperidino, cyclohexylimino, morpholino, thiomorpholino, piperazino, N-methylpiperazino, tetrahydroquinolino or 2-methylindolino.

Acylamino (preferably alkanoylamino) represents, for example, formylamino, acetylamino, propionylamino, n- or iso-butyrylamino, valeroylamino, isovaleroylamino and pivaloylamino.

Alkoxycarbonyl represents, for example, methoxycarbonyl, ethoxycarbonyl, n- or iso-propoxycarbonyl, n-, iso- or tert.-butoxycarbonyl, allyloxycarbonyl or cyclohexyloxycarbonyl.

Aralkyl represents, for example, benzyl, 4-chlorobenzyl, 2,6-dichlorobenzyl, 3-bromobenzyl, 2-methoxybenzyl, 3-hydroxybenzyl, 2,4,6-trimethylbenzyl, phenylethyl, 4-chlorophenylethyl, phenylpropyl or phenylbutyl.

Aryl represents, for example, phenyl, 2-chlorophenyl. 2,4-dichlorophenyl, 3-nitrophenyl, 3-trifluoromethylphenyl, 2-trifluoromethyl-4-chlorophenyl, 2-methylphenyl, 4-ethylphenyl, 3,4-dimethylphenyl, 3-hydroxyphenyl, 2-methoxyphenyl, 4-ethoxyphenyl, 2-methoxy-5-chlorophenyl, 2,5-diethoxyphenyl, 4-aminosulphonylphenyl, 3-dimethylaminophenyl, 3-ethylaminophenyl or 3-ethylamino-4-methylphenyl.

Hetero-aryl represents, for example, furane, thiophene, pyrrole, oxazole, isoxazole, thiazole, pyrazole, imidazole, triazole, pyridine, pyrimidine, thiazine, indole, benzimidazole, benzoxazole, benzthiazole, indazole, quinoline, isoquinoline, quinazoline, quinoxaline, benzotriazine or phthalazine.

Solvents which can be used are all the organic solvents which are inert towards the particular reactants. These include, preferably, aliphatic alcohols, such as methanol, ethanol, isopropanol or butanol, ethers, such as tetrahydrofurane, dioxane, ethylene glycol monomethyl ethers and ethylene glycol diethyl ethers, glycols, such as ethylene glycol, propylene glycol and diethylene glycol, and corresponding ethers with aliphatic alcohols, such as diethylene glycol dimethyl ether, hydrocarbons, such as ligroin, toluene, xylene and tetralin, halogenohydrocarbons, such as chloroform, carbon tetrachloride, chlorobenzene and dichlorobenzenes, nitriles, such as acetonitrile and propionitrile, carboxylic acid amides, such as dimethylformamide and dimethylacetamide, heterocyclic bases, such as pyridine, picolines, collidines, quinoline or isoquinoline, and also commercially available industrial mixtures of these solvents.

The reaction can be carried out under normal pressure, but also under elevated pressure. Elevated pressure can be desirable for the reaction, especially if ammonia or low-boiling primary amines are used as reactants.

The reaction temperature can be varied within a relatively wide range. In general, the reaction is carried out at a temperature of from 20° to 250° C., preferably at from 20° to 180° C., in particular at from 40° to 150° C.

Any of the customary acid-binding agents can be used as the acid-binding agent. These include inorganic bases, such as alkali metal hydroxides and alkaline earth metal hydroxides, for example sodium hydroxide, potassium hydroxide, calcium hydroxide and barium hydroxide, alkali metal carbonates or alkaline earth metal carbonates, such as sodium carbonate, potassium carbonate and calcium carbonate, sodium bicarbonate, potassium bicarbonate and amides, such as alkali metal amides, for example, sodium amide, and organic bases, such as tertiary amines, for example triethylamine, N,N-dimethylaniline, pyridines, quinolines and isoquinolines. Instead of one of the customary acid-binding agents, an excess of the ammonia or primary amine reactant can also be advantageously used in the reaction.

In carrying out the process according to the invention, at least 1 mol of ammonia or primary amine of the formula (III) and at least 1 mol of one of the acid-binding agents mentioned are desirably employed per 1 mol of the 2-alkyl-3-aryl-4H-quinazolin-4-one of the formula (II).

As a rule, in the course of the reaction according to the invention the starting materials dissolve completely or partially, whilst the end products crystallise out. The separating out of the end products can be accelerated by cooling and/or by adding a precipitating agent, such as water, a lower aliphatic ether, such as diethyl ether or dibutyl ether, or a lower aliphatic hydrocarbon, such as petroleum ether or light petrol.

6,7-Dihydro-5H,13H-quinazolino[3,2-a][1,4]benzodiazepine-5,13-diones of the formula (I) in which $R^1$ and $R^5$ are the same or different and each represents 1 or 2 substituents which are the same or different and each of which is hydrogen, halogen, nitro, cyano, trifluoromethyl, amino, alkyl having from 1 to 4 carbon atoms or alkoxy having from 1 to 4 carbon atoms, $R^2$ is hydrogen, alkyl having from 1 to 6 carbon atoms and optionally substituted by phenyl, pyridyl, halogen, alkoxy or di-alkylamino, each of the alkyl and alkoxy moieties containing from 1 to 4 carbon atoms, or an alkoxycarbonyl group having from 1 to 4 carbon atoms in the alkoxy moiety and $R^3$ and $R^4$ are the same or different and each is hydrogen, alkyl having from 1 to 4 carbon atoms or phenyl, are of particular interest.

In detail, specific new active compounds which may be mentioned are: 6,7-dihydro-5H,13H-quinazoline[3,2-a][1,4] benzodiazepine-5,13-dione and 1-chloro-, 2-chloro- . . . 3-chloro-, 4-chloro-, 9-chloro-, 10-chloro-, 11-chloro-, 12-chloro, 1,3-dichloro-, 1,4-dichloro-, 9,11-dichloro, 9,12-dichloro-, 1,2,3-trichloro-, 9,10,11-trichloro-, 1,2,3,4-tetrachloro-, 9,10,11,12-tetrachloro-, 3-bromo-, 11-bromo-, 1,3-dibromo-, 9,11-dibromo-, 3-fluoro-, 11-fluoro-, 1,3-diiodo-, 9,11-diiodo-, 1-trifluoromethyl-, 2-trifluoromethyl-, 3-trifluoromethyl-, 4-trifluoromethyl-, 9-trifluoromethyl-, 10-trifluoromethyl-, 11-trifluoromethyl-, 12-trifluoromethyl-, 1-methyl-, 2-methyl-, 3-methyl-, 9-methyl-, 10-methyl-, 11-methyl-, 2,4-dimethyl-, 10,12-dimethyl-, 1-ethyl-, 9-ethyl-, 1-methoxy-, 3-methoxy-, 4-methoxy-, 9-methoxy-, 11-methoxy-, 12-methoxy-, 2,3-dimethoxy-, 10,11-dimethoxy-, 2-ethoxy-, 10-ethoxy-, 1-hydroxy-, 2-hydroxy-, 9-hydroxy-, 10-hydroxy-, 1-nitro-, 2-nitro-, 3-nitro-, 4-nitro-, 9-nitro-, 10-nitro-, 11-nitro-, 12-nitro, 1,3-dinitro-, 9,11-dinitro-, 1-nitro-3-chloro-, 9-nitro-11-chloro-, 9,11-dinitro-12-chloro-, 1-bromo-3-nitro-, 9-bromo-11-nitro-, 1-amino-, 2-amino-, 3-amino-, 4-amino-, 9-amino-, 10-amino-, 11-amino-, 12-amino-, 1,3-diamino-, 9,11-diamino-, 10-acetylamino-, 11-acetylamino-, 2-ethoxycarbonylamino-, 3-ethoxycarbonylamino-, 11-ethoxycarbonylamino-, 10-dimethylamino-, 10-N-ethyl-N-formylamino-, 10-pyrrolidino-, 10-piperidino-, 10-morpholino-, 10-N-methylpiperazino-, 10-ethylamino-, 10-isopropoxycarbonylamino-, 2-carboxy-, 3-carboxy-, 4-carboxy-, 2-methoxycarbonyl-, 3-ethoxycarbonyl-, 4-butoxycarbonyl-, 2-aminocarbonyl-, 3-butylaminocarbonyl-, 4-morpholinocarbonyl-, 10-aminosulphonyl-, 11-aminosulphonyl-, 10-chloro-11-aminosulphonyl-, 11-methylaminosulphonyl-, 11-diethylaminosulphonyl-, 9-methoxy-11-chloro-12-methyl-, 9-chloro-12-ethyl-, 3,10-dichloro-, 3,11-dichloro-, 2-chloro-11-trifluoromethyl-, 4-chloro-10-trifluoromethyl-, 3,11-bis-tri-fluoromethyl-, 6-methyl-, 6-butyl-, 6-(2-ethoxymethyl)-, 6-(3-dimethylaminoethyl)-, 6-(2-diethylaminoethyl)-, 6-(2-diethylaminopropyl)-, 6-ethoxycarbonylmethyl-, 6-piperidinoethyl-, 6-(4-methylpiperidinoethyl)-, 6-(N-methylpiperazinopropyl)-, 6-morpholinoethyl-, 6-benzyl-, 6-(4-chlorobenzyl)-, 6-(2,4-dichlorobenzyl)-, 6-(3-hydroxybenzyl)-, 6-phenylethyl-, 6-(4-methoxyphenylethyl)-, 6-acetyl-, 6-ethoxycarbonyl-. 6-(picol-2-yl)-, 6-(picol-4-yl)-, 7-methyl-, 7-phenyl-, 7-(3-chlorophenyl)-, 7-thienyl-, 7-methyl-7-(4-chlorophenyl)-, 7-(fur-2-yl)-10-chloro-, 3-chloro-6-benzyl-7-methyl- and 4-chloro-6-ethyl-7-phenyl-11-trifluoromethyl- 6,7-dihydro-6H,13H-quinazolino[3,2-a][1,4]-benzodiazepine-5,13-diones.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol: (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluent (with, of course, the above-mentioned exclusion of solvent having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% especially from 0.5 to 90%, of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is from 5 mg to 25 g, most preferably from 25 mg to 5 g, of active ingredient orally and from 2.5 mg to 10 g, most preferably from 5 mg to 2.5 g of active ingredient parenterally.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

The invention further provides a method of combating (including prevention, relief and cure of) the above mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously or intravenously), rectally or intravaginally, preferably orally or parenterally. Preferred pharmaceutical compositions and medicaments are therefore those adapted for oral or parenteral administration, such as tablets, capsules, pills or dragees, or injection solutions or suspensions respectively. Administration in the method of the invention is preferably orally or parenterally.

In general it has proved advantageous to administer amounts of from 0.1 to 500 mg, preferably from 0.5 mg to 100 mg per kg of body weight per day orally or from 0.05 to 200 mg, preferably from 0.1 to 50 mg, per kg of body weight per day parenterably to achieve effective results. Nevertheless it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, whilst other cases the upper limit mentioned must be exceeded to achieve the desired results. Where larger amounts are administered it can be advisable to divide these into several individual administrations over the course of the day.

These statements apply to using the compounds according to the invention in medicine.

PREPARATION EXAMPLES

EXAMPLE 1

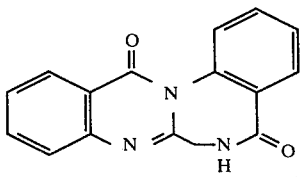

14.7 g (0.05 mol) of 2-bromomethyl-3-(2-methoxycarbonylphenyl)-4H-quinazolin-4-one and 25 ml of liquid ammonia in 100 ml of ethylene glycol monomethyl ether are heated to 100° C. for 5 hours in an autoclave. After cooling the mixture, the colourless crystals are filtered off and washed several times with methanol. 6.1 g (44% theory) of 6,7-dihydro-5H,13H-quinazolino[3,2-a][1,4]benzodiazepine-5,13-dione are obtained.

Melting point: 313°–315° C. (from dimethylformamide).

(a) The reaction product of Example 1 is also obtained, in 69% yield, by reacting 32.9 g (0.1 mol) of 2-chloromethyl-3-(2-methoxycarbonyl-phenyl)-4H-quinazolin-4-one and 80 ml of liquid ammonia in 200 ml of ethylene glycol monomethyl ether at 120° C. for 5 hours in an autoclave.

2-Chloromethyl-3-82-methoxycarbonyl-phenyl)-4H-quinazolin-4-one (melting point: 197°–199° C., recrystallised from toluene) was prepared from N-chloroacetyl-anthranilic acid and anthranilic acid methyl ester analogously to the method in J. pr. Chem. (4) 14 (1961), 84.

(b) The reaction product of Example 1 is also obtained, in 81% yield, by passing gaseous ammonia into a solution of 0.05 mol of 2-chloromethyl-3-(2-methoxycarbonyl-phenyl)-4H-quinazolin-4-one in 250 ml of dimethylformamide at 20°–25° C. for 2 hours and leaving the mixture to stand for 12 hours.

EXAMPLE 2

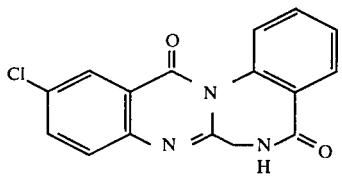

18.9 g (0.05 mol) of 2-chloromethyl-3-(2-ethoxycarbonylphenyl)-6-chloro-4H-quinazolin-4-one and 50 ml of liquid ammonia in 150 ml of ethylene glycol monoethyl ether are heated to 60° C. for 3 hours in an autoclave. After cooling the mixture, the colourless crystals are filtered off and washed several times with methanol. 13 g (83% of theory) of 11-chloro-6,7-dihydro-5H,13H-quinazolino[3,2-a][1,4]benzodiazepine-5,13-dione are obtained.

Melting point: 286°–288° C. (from dimethylformamide/ethanol, 1:1).

2-Chloromethyl-3-(2-ethoxycarbonyl-phenyl)-6-chloro-4H-quinazolin-4-one (melting point: 195°–197° C., recrystallised from toluene) was prepared from N-chloroacetyl-5-chloroanthranilic acid and anthranilic acid ethyl ester analogously to the method in J. Amer. Chem. Soc. 68 (1946), 542.

EXAMPLE 3

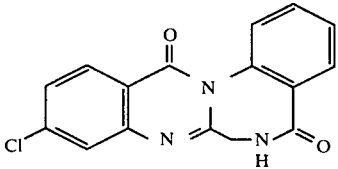

Analogously to Example 1(a), 18 g (0.05 mol) of 2-chloromethyl-3-(2-methoxycarbonyl-phenyl)-7-chloro-4H-quinazolin-4-one (melting point: 150°–152° C. from ethanol) and 50 ml of liquid ammonia in 150 ml of ethylene glycol monomethyl ether give, at 80° C. in the course of 5 hours, 10 g (65% of theory) of 10-chloro-6,7-dihydro-5H,13H-quinazolino[3,2-a][1,4]benzodiazepine-5,13-dione.

Melting point: 290°–292° C. (from dimethylformamide).

EXAMPLE 4

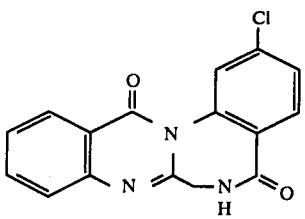

Analogously to Example 1(a), 18 g (0.05 mol) of 2-chloromethyl-3-(2-methoxycarbonyl-5-chlorophenyl)-4H-quinazolin-4-one (melting point: 151°–152° C. from ethanol) and 50 ml of liquid ammonia in 150 ml of ethylene glycol monomethyl ether give, at 80° C. in the course of 5 hours, 9.5 g (61% of theory) of 2-chloro 6,7-dihydro-5H-13H-quinazolino[3,2-a][1,4]benzodiapezine-5,13-dione.

Melting point: 330°–333° C. (from dimethylformamide).

EXAMPLE 5

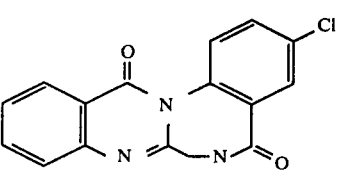

Analogously to Example 1(a), 18 g (0.05 mol) of 2-chloromethyl-3-(2-methoxycarbonyl-4-chlorophenyl)-4H-quinazolin-4-one (melting point: 135°–136° C. from toluene) and 50 ml of liquid ammonia in 150 ml of ethylene glycol monomethyl ether give, at 80° C. in the course of 5 hours, 13 g (84% of theory) of 3-chloro-6,7-dihydro-5H,13H-quinazolino[3,2-a][1,4]benzodiazepin-5,13-dione.

Melting point 294°–296° C. (from dimethylformamide).

EXAMPLE 6

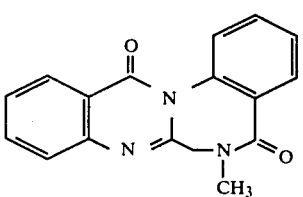

16.4 g (0.05 mol) of 2-chloromethyl-3-(2-methoxycarbonyl-phenyl)-4H-quinazolin-4-one and 10 ml of liquid methylamine in 100 ml of ethylene glycol monomethyl ether are heated to 40° C. for 2 hours in an autoclave. After cooling the mixture, the colourless crystals are filtered off and washed several times with ethanol. 12 g (82.5% of theory) of 6-methyl-6,7-dihydro-5H,13H-quinazolino[3,2-a][1,4]benzodiazepine-5,13-dione are obtained.

Melting point: 204°–206° C. (from ethanol).

EXAMPLE 7

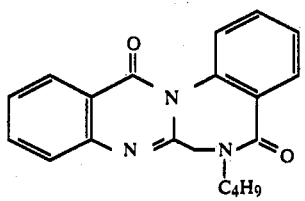

Analogously to Example 6, 32.9 g (0.1 mol) of 2-chloromethyl-3-(2-methoxycarbonyl-phenyl)-4H-quinazolin-4-one and 75 ml of n-butylamine in 200 ml of ethylene glycol monomethyl ether give, at 120° C. in the course of 5 hours, 7 g (21% of theory) of 6-n-butyl-6,7-dihydro-5H,13H-quinazolino[3,2-a][1,4]benzodiazepine-5,13-dione.

Melting point: 125°–127° C. (from ethanol).

EXAMPLE 8

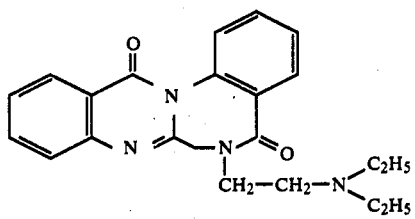

16.4 g (0.05 mol) of 2-chloromethyl-3-(2-methoxycarbonyl-phenyl)-4H-quinazolin-4-one and 12.8 g (0.11 mol) of 1-amino-2-dimethylamino-ethane in 100 ml of ethylene glycol monomethyl ether are heated to 120° C. for 5 hours. The solvent is evaporated off on a Rotavapor and 50 ml of ethanol are added to the oil residue. A clear solution is formed, and after a short time colourless crystals separated out. 12.4 g (66% of theory) of analytically pure 6-diethylaminoethyl-6,7-dihydro-5H,13H-quinazolino[3,2-a][1,4]-benzodiazepine-5,13-dione are obtained by filtering off the crystals and washing them with ethanol and water.

Melting point: 117°–119° C.

EXAMPLE 9

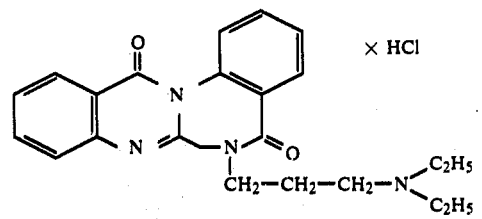

16.4 g (0.05 mol) of 2-chloromethyl-3-(2-methoxycarbonyl-phenyl)-4H-quinazolin-4-one and 14.3 g (0.11 mol) of 1-amino-3-diethylamino-propane in 100 ml of ethylene glycol monomethyl ether are heated to 120° C. for 5 hours. The solvent is evaporated off on a Rotavapor and 50 ml of water and 100 ml of chloroform are added to the oil residue. After separating off the chloroform phase in a separating funnel, this is extracted by shaking with water, dilute sodium hydroxide solution and again with water, and dried over sodium sulphate and the chloroform is evaporated off on a Rotavapor. The oil residue is dissolved in ethanol, and hydrogen chloride is passed in until the solution becomes saturated. Analytically pure 6-diethylaminopropyl-6,7-dihydro-5H,13H-quinazolino[3,2-a][1,4]benzodiazepine-5,13-dione hydrochloride thereby crystallises out (15.1 g, 71% of theory).

Melting point: 237°–238° C.

EXAMPLE 10

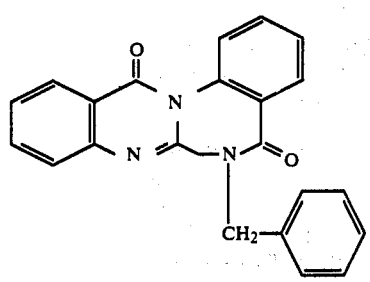

Analogously to Example 1(a), 30 g (0.091 mol) of 2-chloromethyl-3-(2-methoxycarbonyl-phenyl)-4H-quinazolin-4-one and 50 ml of benzylamine in 200 ml of ethylene glycol monomethyl ether give, at 120° C. in the course of 5 hours, 29.5 g (88% of theory) of 6-benzyl-6,7-dihydro-5H,13H-quinazolino[3,2-a][1,4]benzodiazepine-5,13-dione.

Melting point: 171°–173° C.

EXAMPLE 11

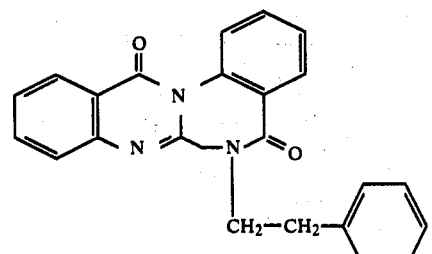

16.4 g (0.05 mol) of 2-chloromethyl-3-(2-methoxycarbonyl-phenyl)-4H-quinazolin-4-one and 12.1 g (0.1 mol) of 2-phenylethylamine in 100 ml of ethylene glycol monomethyl ether are heated to 100° C. for 5 hours. The solvent is evaporated off on a Rotavapor and 100 ml of water are added to the semi-solid residue. The colourless crystals are filtered off and washed with hot methanol. 5.8 g (30.5% of theory) of 6-(2-phenylethyl)-6,7-dihydro-5H,13H-quinazolino[3,2-a][1,4]benzodiazepine-5,13-dione are obtained.

Melting point: 208°–210° C.

EXAMPLE 12

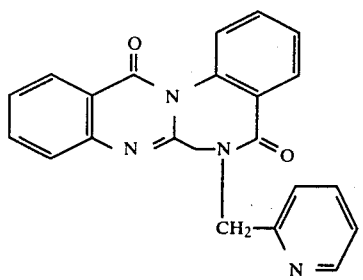

16.4 g (0.05 mol) of 2-chloromethyl-3-(2-methoxycarbonyl-phenyl)-4H-quinazolin-4-one and 12 g (0.11 mol) of 2-aminomethylpyridine in 100 ml of ethylene glycol monomethyl ether are heated to 120° C. for 5 hours. The solvent is evaporated off on a Rotavapor and the solid residue is recrystallised from methanol. After filtering off the crystals, they are washed with methanol and water, whereupon 10 g (54.5% of theory) of 6-(pyrid-2-yl-methyl)-6,7-dihydro-5H,13H-quinazolino[3,2-a][1,4]benzodiazepine-5,13-dione are obtained.

Melting point: 202°–203° C.

EXAMPLE 13

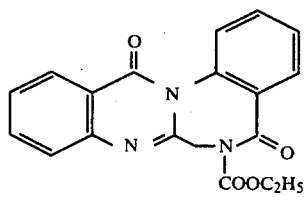

8 g (0.029 mol) of the reaction product from Example 1 in 30 ml of pyrocarbonic acid diethyl ester are heated to 120° C. for 15 minutes, the ethanol which forms being continuously distilled off via a descending condenser. Ethanol and excess diethyl pyrocarbonate are evaporated off on a Rotavapor and a further 50 ml of ethanol are added to the oil residue. Colourless crystals form which, after being filtered off, are washed with ethanol. 6.4 g (63.5% of theory) of 6-ethoxycarbonyl-6,7-dihydro-5H,13H-quinazolino[3,2-a][1,4]benzodiazepine-5,13-dione are obtained.

Melting point: 185°–187° C.

EXAMPLE 14

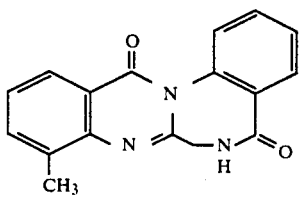

Analogously to Example 1(a), 0.05 mol of 2-chloromethyl-3-(2-methoxycarbonyl-phenyl)-8-methyl-4H-quinazolin-4-one (melting point 206°–208°) and 50 ml of liquid ammonia in 150 ml of ethylene glycol diethyl ether give, at 60° in the course of 3 hours, 76% of theory of 9-methyl A.*)

*) The abbreviation A used in most of the examples means: 6,7-dihydro-5H,13H-quinazolino[3,2-a][1,4]benzodiazepine-5,13-dione Melting point 273°–274° (from n-butanol).

EXAMPLE 15

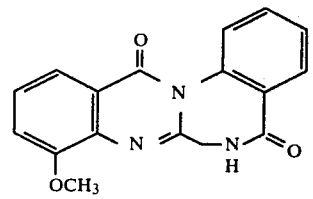

Analogously to Example 1(a), 0.05 mol of 2-chloromethyl-3 (2-methoxycarbonyl-phenyl)-8-methoxy-4H-quinazolin-4-one (melting point 208°–210°) and 50 ml of liquid ammonia in 150 ml of n-butanol give, at 60° in the course of 3 hours, 52% theory of 9-methoxy-A.

Melting point 290°–292° (from n-butanol).

EXAMPLE 16

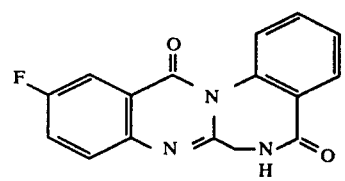

Analogously to Example 1(a), 0.135 mol of 2-chloromethyl-3-(2-methoxycarbonyl-phenyl)-6-fluoro-4H-quinazolin-4-one (melting point 213°–215°) in 400 ml of ethylene glycol and 140 ml of liquid ammonia give, at 60° in the course of 3 hours, 85% of theory of 11-fluoro-A.

Melting point 275°–277° (from ethylene glycol monomethyl ether).

EXAMPLE 17

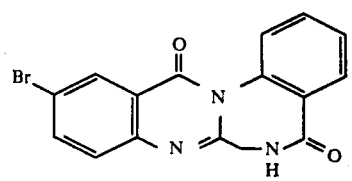

Analogously to Example 1(a), 0.05 mol of 2-chloromethyl-3-(2-methoxycarbonyl-phenyl)-6-bromo-4H-quinazolin-4-one (melting point 235°–237°) and 50 ml of liquid ammonia in 150 ml of pyridine give, at 60° in the course of 5 hours, 88% of theory of 11-bromo-A.

Melting point 300°–303°.

EXAMPLE 18

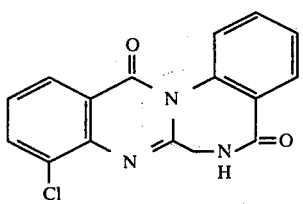

Analogously to Example 1(a), 0.025 mol of 2-chloromethyl 3-(2-methoxycarbonyl-phenyl)-8-chloro-4H-quinozalin-4-one (melting point 205°–208°) and 20 ml of liquid ammonia in 50 ml of ethylene glycol monoethyl ether give, at 50° in the course of 3 hours, 71% of theory of 9-chloro-A.

Melting point 255°–258°.

EXAMPLE 19

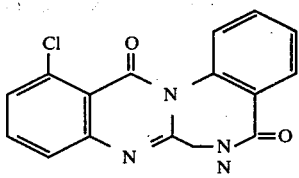

Analogously to Example 1(a), 0.05 mol of 2-chloromethyl-3-(2-methoxycarbonyl-phenyl)-5-chloro-4H-quinazolin-4-one (melting point 177°–178°) and 50 ml of liquid ammonia in 150 ml of ethylene glycol dimethyl ether give, at 60° in the course of 3 hours, 60% of theory of 12-chloro-A.

Melting point 308°–310° (from dimethylformamide).

EXAMPLE 20

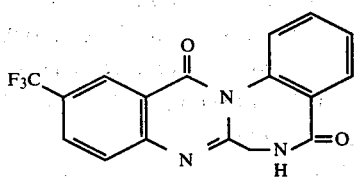

Analogously to Example 1(a), 0.05 mol of 2-chloromethyl-3-(2-methoxycarbonyl-phenyl)-6-trifluoromethyl-4H-quinazolin-4-one (melting point 169°–170°) and 50 ml of liquid ammonia in 150 ml of dioxane give, at 50° in the course of 3 hours, 36% of theory of 11-trifluoromethyl-A.

Melting point 190°–192° (from toluene).

EXAMPLE 21

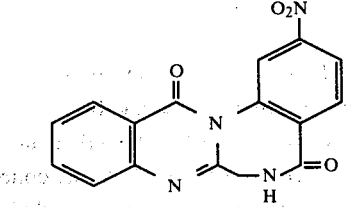

Analogously to Example 1(a), 0.05 mol of 2-chloromethyl-3-(2-methoxycarbonyl-5-nitro-phenyl)-4H-quinazolin-4-one (melting point 158°–159°) and 50 ml of liquid ammonia in 150 ml of o-dichlorobenzene give, at 60° in the course of 3 hours, 35% of theory of 2-nitro-A.

Melting point 276°–277°, decomposition (from glacial acetic acid).

EXAMPLE 22

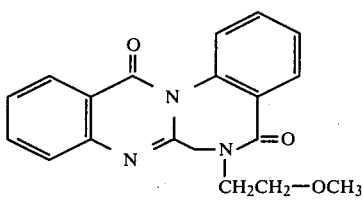

Analogously to Example 8, 0.05 mol of 2-methoxymethyl-3-(2-methoxycarbonyl-phenyl)-4H-quinazolin-4-one (melting point 134°–137°, prepared from 2-bromomethyl-3-(2-methoxycarbonyl-phenyl)-4H-quinazolin-4-one and methanol analogously to the method in J. Med. Chem. 20, 379 (1977)) and 20 ml of 2-methoxyethylamine in 100 ml of ethanol give, at 50° in the course of 3 hours, 40% of theory of 6-methoxyethyl-A.

Melting point 127°–130° (from ethanol).

EXAMPLE 23

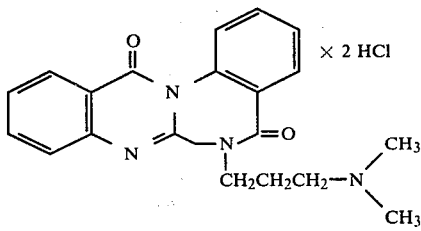

Analogously to Example 9, 0.05 mol of 2-chloromethyl-3-(2-ethoxycarbonyl-phenyl)-4H-quinazolin-4-one and 10 g of 3-dimethylaminopropylamine in 100 ml of ethylene glycol monoethyl ether give, at 120° in the course of 5 hours, 67% of theory of 6-dimethylaminopropyl-A dihydrochloride.

Melting point 198°–200° (from ethanol).

EXAMPLE 24

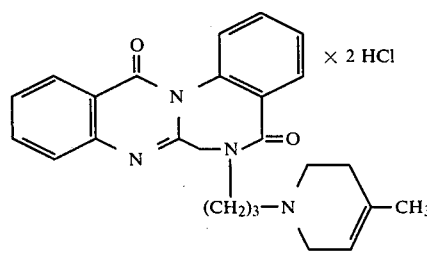

Analogously to Example 9, 0.05 mol of 2-chloromethyl-3-(2-ethoxycarbonyl-phenyl)-4H-quinazolin-4-one and 17 g of N-aminopropyl-4-methyl-1,2,5,6-tetrahydro-pyridine in 100 ml of tetralin give, at 120° in the course of 5 hours, 45% of theory of 6-(4- methyl-1,2,5,6-tetrahydro-pyridino-propyl)-A dihydrochloride.

Melting point 112°–115° (from ethanol).

EXAMPLE 25

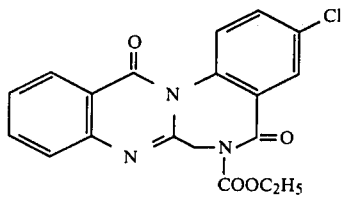

Analogously to Example 13, 0.05 mol of the reaction product from Example 5 and 60 ml of pyrocarbonic acid diethyl ester give, at 120°–130° in the course of 20 minutes, 80% of theory of 6-ethoxycarbonyl-3-chloro-A.

Melting point 189°–191° (from ethanol).

EXAMPLE 26

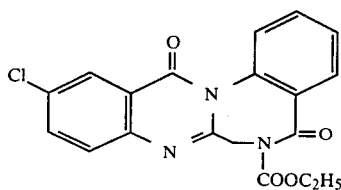

Analogously to Example 13, 0.015 mol of the reaction product from Example 2 and 20 ml of pyrocarbonic acid diethyl ester give, at 130°–135° in the course of 30 minutes, 94% of theory of 6-ethoxycarbonyl-11-chloro-A.

Melting point 258°–260° (from ethanol).

EXAMPLE 27

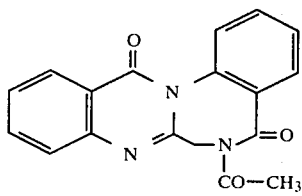

0.05 mol of the reaction product from Example 1 in 100 ml of acetic acid anhydride and 10 ml of pyridine are heated to 120° for 8 hours. After cooling the mixture, the clear solution is poured on to water and the crystals which have precipitated are filtered off. 44% of theory of 6-acetyl-A are obtained.

Melting point 189°–191° (from ethanol).

EXAMPLE 28

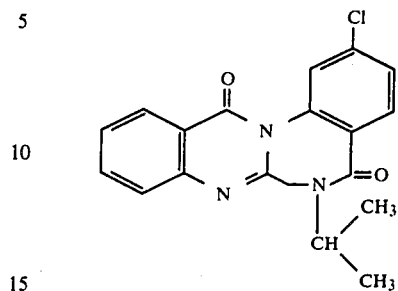

Analogously to Example 1(a), 0.03 mol of 2-chloromethyl 3-(2-methoxycarbonyl-5-chlorophenyl)-4H-quinazolin-4-one and 25 ml of isopropylamine (65% strength solution in water) in 100 ml of isopropanol give, at 50° in the course of 3 hours 48% of theory of 2-chloro-6-isopropyl-A.

Melting point 195° (from ethanol).

EXAMPLE 29

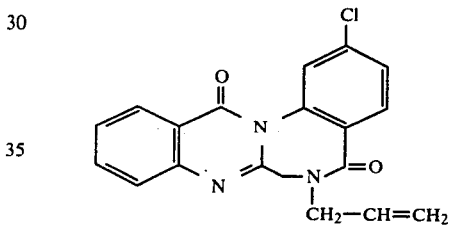

Analogously to Example 1(a), 0.03 mol of 2-chloromethyl 3-(2-methoxycarbonyl-5-chlorophenyl)-4H-quinazolin-4-one and 15 ml of allylamine in 100 ml of toluene give, at 50° in the course of 3 hours, 89% of theory of 6-allyl-2-chloro-A.

Melting point 155°–157°.

EXAMPLE 30

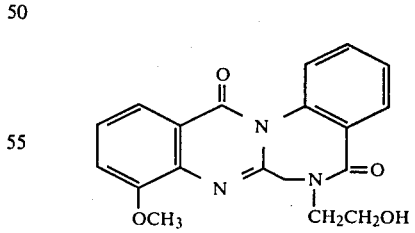

Analogously to Example 8, 0.035 mol of 2-chloromethyl-3-(2-methoxycarbonyl-phenyl)-8-methoxy-4H-quinazolin-4-one and 15 ml of ethaolamine in 100 ml of propylene glycol give, at 80° in the course of 5 hours, 80.5% of theory of 6-hydroxyethyl-9-methoxy-A.

Melting point 233°–235°.

EXAMPLE 31

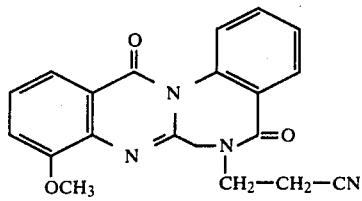

Analogously to Example 8, 0.035 mol of 2-chloromethyl-3-(2-methoxycarbonyl-phenyl)-8-methoxy-4H-quinazolin-4-one and 15 ml of cyanoethylamine in 100 ml of ethanol give, at 80° in the course of 5 hours, 51% of theory of 6-cyanoethyl-9-methoxy-A.

Melting point 198°–200° (from ethanol).

EXAMPLE 32

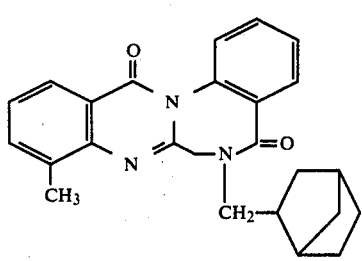

Analogously to Example 8, 0.03 mol of 2-chloromethyl-3-(2-methoxycarbonyl-phenyl)-8-methyl-4H-quinazolin-4-one and 15 ml of 2-norbornylamine in 100 ml of ethylene glycol monomethyl ether give, at 80° in the course of 5 hours, 62% of theory of 6-norborn-2-yl-9-methyl-A.

Melting point 168°–169° (from methanol).

EXAMPLE 33

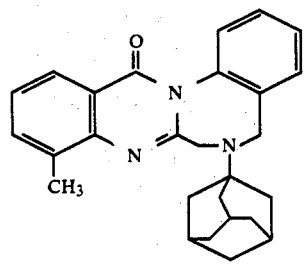

Analogously to Example 8, 0.03 mol of 2-chloromethyl-3-(2-methoxycarbonyl-phenyl)-8-methyl-4H-quinazolin-4-one and 0.07 mol of 1-aminoadamantane in 100 ml of ethylene glycol monoethyl ether give, at 125°–130° in the course of 5 hours, 90% of theory of 6-adamant-1-yl-9-methyl-A.

Melting point 204°–206°.

EXAMPLE 34

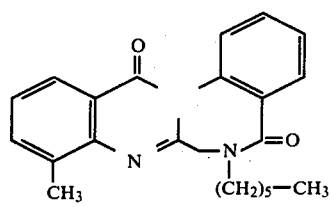

Analogously to Example 8, 0.03 mol of 2-chloromethyl-3-(2-methoxycarbonyl-phenyl)-8-methyl-4H-quinazolin-4-one and 15 ml of n-hexylamine in 100 ml of n-butanol give, at 80° in the course of 5 hours, 88.5% of theory of 6-hexyl-9-methyl-A. Melting point 138°–139°.

EXAMPLE 35

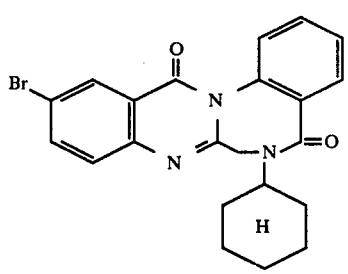

Analogously to Example 8, 0.05 mol of 2-chloromethyl-3-(2-methoxycarbonyl-phenyl)-6-bromo-4H-quinazolin-4-one and 20 ml of cyclohexylamine in 100 ml of ethylene glycol give at 125° in the course of 5 hours, 43% of theory of 11-bromo-6-cyclohexyl-A Melting point 276°–279°.

EXAMPLE 36

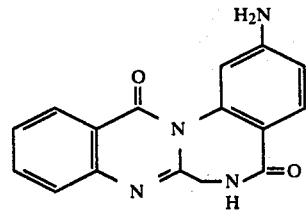

0.06 mol of the reaction product from Example 21 is hydrogenated in 150 ml of dimethylformamide at 60° in the presence of 5 g of Raney nickel. After filtering off the catalyst, the solution is evaporated (Rotavapor) and the residue is extracted hot with ethylene glycol monomethyl ether. On cooling the extract, analytically pure 2-amino-A crystallises out.

Yield 50% of theory, melting point >340°.

EXAMPLE 37

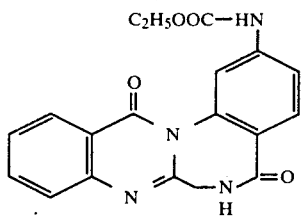

0.015 mol of the reaction product from Example 36 in 100 ml of ethanol is heated to 80° with 10 g of pyrocarbonic acid diethyl ester for 12 hours. After cooling the mixture and filtering off the precipitate and washing it with ethanol. 89% of theory of 2-ethoxycarbonylamino-A are obtained.

Melting point 335°, decomposition.

What is claimed is:

1. A compound which is a 6,7-Dihydro-5H, 13H-quinazolin [3,2-a][1,4]benzodiazepine-5,13-dione of the formula (I) or its pharmacologically acceptable acid-addition salts:

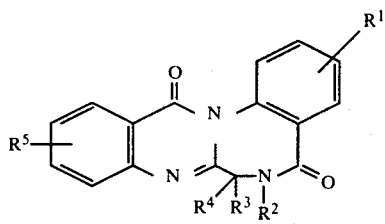

in which $R^1$ and $R^5$ are the same or different and each represents 0, 1, 2, 3 or 4 substituents which are the same or different and each of which is alkyl, hydroxyl, acyloxy, alkoxy, nitro, amino, alkylamino, dialkylamino, acylamino, acylalkylamino, alkoxycarbonylamino, halogen, trifluoromethyl, cyano, carboxyl, alkoxycarbonyl, aminocarbonyl, alkylaminocarbonyl, dialkylaminocarbonyl, aminosulphonyl, alkylaminosulphonyl, dialkylaminosulphonyl, alkylaminocarbonylamino or dialkylaminocarbonylamino, each of said alkyl, alkoxy and acyl radicals having 1 to 4 carbon atoms $R^2$ is hydrogen, alkyl having from 1 to 6 carbon atoms and optionally substituted by phenyl, pyridyl, halogen, alkoxy or dialkylamino, each of the alkyl and alkoxy moieties containing from 1 to 4 carbon atoms, or an alkoxycarbonyl group having from 1 to 4 carbon atoms in the alkoxy moiety and $R^3$ and $R^4$ are the same or different and each is hydrogen, alkyl having from 1 to 4 carbon atoms or phenyl.

2. A compound according to claim 1 in which $R^1$ and $R^5$ are the same or different and each represents 0, 1 or 2 substituents which are the same of different and each of which is halogen, nitro, cyano, trifluoromethyl, amino, alkyl having from 1 to 4 carbon atoms or alkoxy having from 1 to 4 carbon atoms, $R^2$ is hydrogen, alkyl having from 1 to 6 carbon atoms and optionally substituted by phenyl, pyridyl, halogen, alkoxy or dialkylamino, each of the alkyl and alkoxy moieties containing from 1 to 4 carbon atoms, or an alkoxycarbonyl group having from 1 to 4 carbon atoms in the alkoxy moiety and $R^3$ and $R^4$ are the same or different and each is hydrogen, alkyl having from 1 to 4 carbon atoms or phenyl.

3. A compound according to claim 1 in which $R^3$ and $R^4$ are hydrogen.

4. A compound according to claim 1 in which $R^1$ and $R^5$ are the same or different and each is hydrogen or halogen, $R^2$ is hydrogen, alkyl having from 1 to 6 carbon atoms or an alkoxy carbonyl group having from 1 to 4 carbon atoms in the alkoxy moiety and $R^3$ and $R^4$ are hydrogen.

5. The compound according to claim 1 which is 6,7-dihydro-5H,13H-quinazolino[3,2-a][1,4]benzodiazepine-5,13-dione.

6. The compound according to claim 1 which is 2-chloro-6,7-dihydro-5H-13H-quinazolino 3,2-a 1,4 benzodiazepine-5,13-dione.

7. The compound according to claim 1 which is 6-ethoxycarbonyl-6,7-dihydro-5H,13H-quinazolino 3,2-a 1,4 benzodiazepine-5,13-dione.

8. A process for the production of a compound according to claim 1 which comprises reacting 2-alkyl-3-aryl-4H-quinazolin-4-one of the formula (II) or an acid-additon salt thereof:

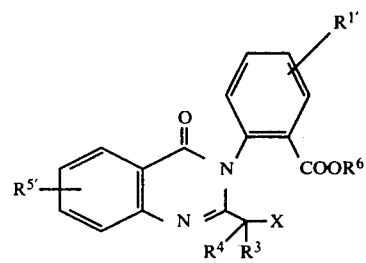

in which $R^3$ and $R^4$ have the same meaning as defined hereinbefore in claim 1, formula (I), $R^{1'}$ and $R^{5'}$ are the same or different and each represents 0, 1, 2, 3 or 4 substituents which are the same or different and each of which is alkyl, hydroxyl, acyloxy, alkoxy, nitro, dialkylamino, heterocycloalkyl containing at least one nitrogen atom in the ring through which it is bonded, acylamino, acylalkylamino, alkoxycarbonylamino, halogen, trifluoromethyl, cyano, alkoxycarbonyl, dialkylaminocarbonyl, aminosulphonyl, alkylaminosulphonyl, dialkylaminosulphonyl and dialkylaminocarbonylamine each of said alkyl, alkoxy and acyl radicals having 1 to 4 carbon atoms, $R^6$ is hydrogen, $C_1$-$C_2$ alkyl, benzyl or phenyl and X is a leaving group which can be replaced nucleophillically, with an amine of the following formula (III) or an acid-addition salt thereof:

$$H_2N-R^{2'} \qquad (III)$$

in which $R^{2'}$ is hydrogen, alkyl having from 1 to 6 carbon atoms and optionally substituted by phenyl, pyridyl, halogen, alkoxy or dialkylamino, each of the alkyl and alkoxy moieties containing from 1 to 4 carbon atoms, or an alkoxycarbonyl group having from 1 to 4 carbon atoms in the alkoxy moiety and $R^1$ and/or $R^5$ is amino, alkylamino, carboxyl, aminocarbonyl, alkylaminocarbonyl or alkylaminocarbonylamino a said corresponding compound of formula I in which $R^1$ and/or $R^5$ is nitro or acylamino, acylalkylamino, alkoxycarbonyl, and/or cyano, or amino, respectively is converted thereto, and in the case of a compound of formula I in which $R^2$ is acyl or alkoxycarbonyl a said corresponding compound of formula I in which $R^2$ is hydrogen is converted thereto.

9. A process according to claim 8 in which the reaction is carried out at from 20° to 250° C.

10. A process according to claim 8 in which the reaction is carried out in the presence of an acid-binding agent.

11. A process according to claim 8 in which the reaction is carried out in the presence of an inert solvent.

12. A pharmaceutical composition containing as an active ingredient an amount effective for providing central nervous system action of a compound according to claim 1 in admixture with a solid or liquefied gaseous diluent or in admixture with a solid or liquefied gaseous diluent or in admixture with a liquid diluent other than a solvent of a molecular weight less than 200 except in the presence of a surface-active agent.

13. A pharmaceutical composition of claim 12 in the form of a sterile or physiologically isotonic aqueous solution.

14. A composition according to claim 12 containing from 0.5 to 95% by weight of the said active ingredient.

15. A medicament in dosage unit form comprising an amount effective for providing central nervous system action of a compound of claim 1 and an inert pharmaceutical carrier.

16. A medicament of claim 15 in the form of tablets, pills, dragees, capsules, ampoules, or suppositories.

17. A medicament in dosage unit form comprising an amount effective for providing central nervous sytem action of a compound of claim 4 and in inert pharmaceutical carrier.

18. A method of treating the central nervous system in warm-blooded animals which comprises administering to the said animals an amount effective for providing central nervous system action of an active compound according to claim 1 either alone or in admixture with a diluent or in the form of a medicament.

19. A method according to claim 18 in which the active compound is administered in an amount of from 0.1 to 500 mg per kg body weight per day.

20. A method according to claim 18 in which the animals are ruminants.

21. A method according to claim 18 in which the active compound is administered orally.

* * * * *

UNITED STATES PATENT AND TRADEMARK OFFICE
CERTIFICATE OF CORRECTION

PATENT NO. : 4,187,306

DATED : February 5, 1980

INVENTOR(S) : Karl Heinrich Mayer, et al.

It is certified that error appears in the above-identified patent and that said Letters Patent are hereby corrected as shown below:

In the abstract, Formula " 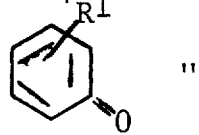 "

delete " $\diagdown 0$ ".

Column 15, line 9 Delete "8" and replace with --C--.

Column 24, line 62 "ethaolamine" should be --ethanolamine--.

Column 27, line 60, claim 2, --same or different-- not same of different.

Signed and Sealed this

Twenty-seventh Day of May 1980

[SEAL]

Attest:

SIDNEY A. DIAMOND

Attesting Officer

Commissioner of Patents and Trademarks